(12) United States Patent
Truckai et al.

(10) Patent No.: US 6,485,436 B1
(45) Date of Patent: Nov. 26, 2002

(54) PRESSURE-ASSISTED BIOPSY NEEDLE APPARATUS AND TECHNIQUE

(76) Inventors: Csaba Truckai, 19566 Arden Ct., Saratoga, CA (US) 95070; Bruno Strul, 485 Cervantes Rd., Portola Valley, CA (US) 94028; John H. Shadduck, 1490 Vistazo West, Tiburon, CA (US) 94920

( * ) Notice: Subject to any disclaimer, the term of this patent is extended or adjusted under 35 U.S.C. 154(b) by 0 days.

(21) Appl. No.: 09/637,463

(22) Filed: Aug. 10, 2000

(51) Int. Cl.$^7$ .............................................. A61B 5/00
(52) U.S. Cl. ...................................................... 600/564
(58) Field of Search ................................ 600/562, 563, 600/564–567; 606/167, 170

(56) References Cited

U.S. PATENT DOCUMENTS 4,966,162 A * 10/1990 Wang .......................... 600/750
4,982,739 A * 1/1991 Hemstreet et al. ........... 600/563
5,285,795 A * 2/1994 Ryan et al. ................... 600/563
5,775,333 A * 7/1998 Burbank et al. .............. 600/567

* cited by examiner

Primary Examiner—Max Hidenburg (57) ABSTRACT

An improved biopsy needle assembly for efficient removal of multiple biopsy cores from a single needle penetration. The needle apparatus comprises an elongate assembly of paired sleeves with an open notch in the wall of the outer sleeve for engaging a tissue volume in the bore of that sleeve. An inner sleeve or blade member with a sharp blade edge is moveable from a retracted position to an extended position to both (i) excise the tissue volume, and (ii) function as valve means to alter the open notch between an open position and a closed position. The invention provides a looped inflow-outflow passageway system for using high-pressure fluid flows to push or expel the excised tissue from the bore in working end where the excised tissue is captured. The looped passageway system is coupled to a remote pressurization source.

19 Claims, 8 Drawing Sheets

PRESSURE-ASSISTED BIOPSY NEEDLE APPARATUS AND TECHNIQUE

FIELD OF THE INVENTION

This invention relates to a medical devices and techniques, and more particularly to a biopsy needle-type probe that is adapted for cutting and removing multiple tissue cores from a single needle penetration, with the tissue extraction accomplished by a looped flow of high-pressure media.

BACKGROUND OF THE INVENTION

To biopsy tissue from a targeted site in the interior of a patient's body, for example in a breast biopsy, the various prior art methods include (i) use of a biopsy needle; (ii) fine needle aspiration in a stereoatatic needle localizing assembly, or (iii) a skin incision and surgical removal of tissue from the targeted site. When using a biopsy needle, such as a True-Cut® needle, the tissue sample is often smaller than desired for biopsy purposes. Fine needle aspiration using a standard 14 Ga. needle also results in small tissue samples. Open skin incisions are undesirable due to scarring.

What is needed is a tissue cutting probe (i) that can excise and remove tissue through a very small diameter needle probe to provide a minimally invasive procedure; (ii) that can take multiple cores from a single needle penetration; (iii) that can be used manually or m conjunction with a stereotactic locking systen; (iv) that can be scaled upward in dimension to perform a stereotactic lumpectomy procedure by successive removal of tissue cores; and (v) that is inexpensive to manufacture and is therefore disposable.

SUMMARY OF THE INVENTION

The present invention comprises an elongate sleeve assembly that can be introduced into the interior of a patient's body for excising and removing small tissue volumes in a minimally invasive procedure. The system of the invention provides a novel pressurization system that uses high positive fluid pressures to push excised tissue from the working end of a probe, in contrast to prior art systems that attempt to pull or aspirate tissue from a working end. The use of high pressure fluid flows to carry tissue along a passageway allows for a very small diameter tissue-extracting lumen. The prior art vacuum sources cannot develop sufficiently strong suction forces to move an excised tissue core within a small diameter tissue-extracting lumen.

In a preferred embodiment, the system provides an elongate needle-type member that carries a looped inflow-outflow passageway system. The distal working end of the needle assembly has a tissue-receiving opening in a wall surrounding a distalmost chamber of a passageway that receives a tissue volume pressed into the opening. A moveable blade member cooperates with the opening to excise the tissue volume captured in the tissue-receiving opening. At the same time, the blade member functions as a valve to alter the opening between a first open position and said second closed position. The looped passageway system comprises (i) an outflow passageway extending between a proximal open end (in the needle handle) and the distalmost chamber thereof, and (ii) an inflow passageway extending between an open proximal end (in the needle handle) and a distal terminus thereof that communicates with the distalmost chamber of the outflow passageway. The pressurization source is connected to the proximal end of the inflow passageway.

In operation, the needle is introduced to the targeted site and the blade member is thereafter actuated to excise tissue engaged within the tissue-receiving opening. The blade member is maintained in the second position which closes off the tissue-receiving opening. The pressurization source is then actuated which delivers a pulse of high pressure fluid flow through the looped inflow and outflow passageways to push the excise tissue from the needle into a collector at the exterior of the patient's body. The excising and extracting steps can be repeated to obtain successive tissue cores from the targeted site with the needle only penetrating to the site once.

The present invention advantageously utilizes positive pressure media flows to transport tissue cores along a very small diameter tissue-extracting lumen, rather than using a negative pressure (vacuum) which has limited effectiveness in a small diameter lumen.

The present invention advantageously can extract multiple tissue cores from a single needle penetration.

The present invention can be coupled to a stereotactic needle localizing assembly for excising relatively large tissue volumes, as in a lumpectomy procedure.

Additional objects and advantages of the invention will be apparent from the following description, the accompanying drawings and the appended claims.

DETAILED DESCRIPTION OF THE INVENTION

1. Type "A" Pressure-Assisted Needle Biopsy System

Figure 1:
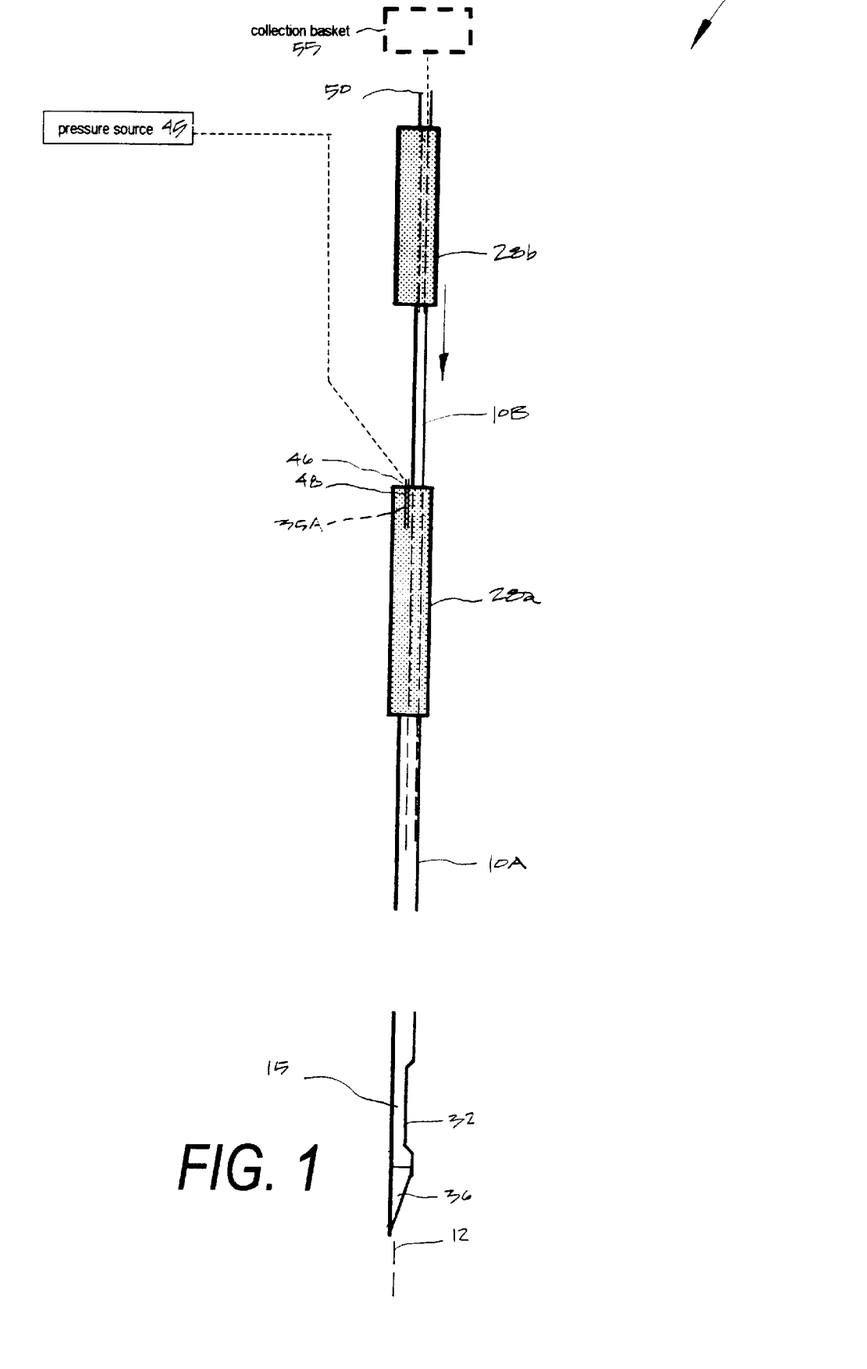
FIG. 1 is a side view of an exemplary Type "A" biopsy needle of the present invention that is adapted for surgical removal of core of tissue, together with a block diagram of a pressure source.
Figure 2A:
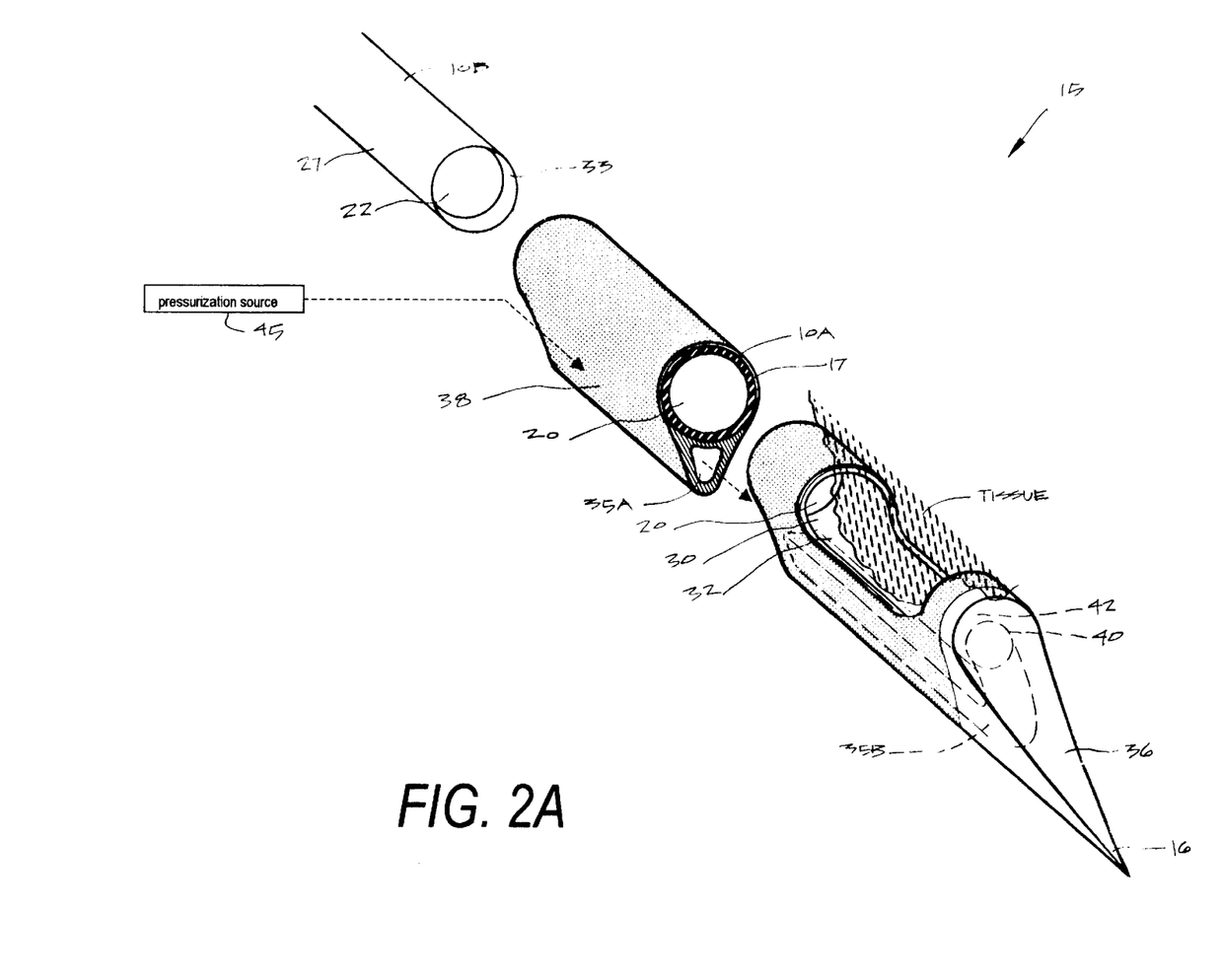
FIG. 2A is an exploded cut-away view of the working end of the biopsy needle of FIG. 1 in a first position engaging tissue and showing the looped inflow-outflow passageway system of the invention.
Figure 2B:
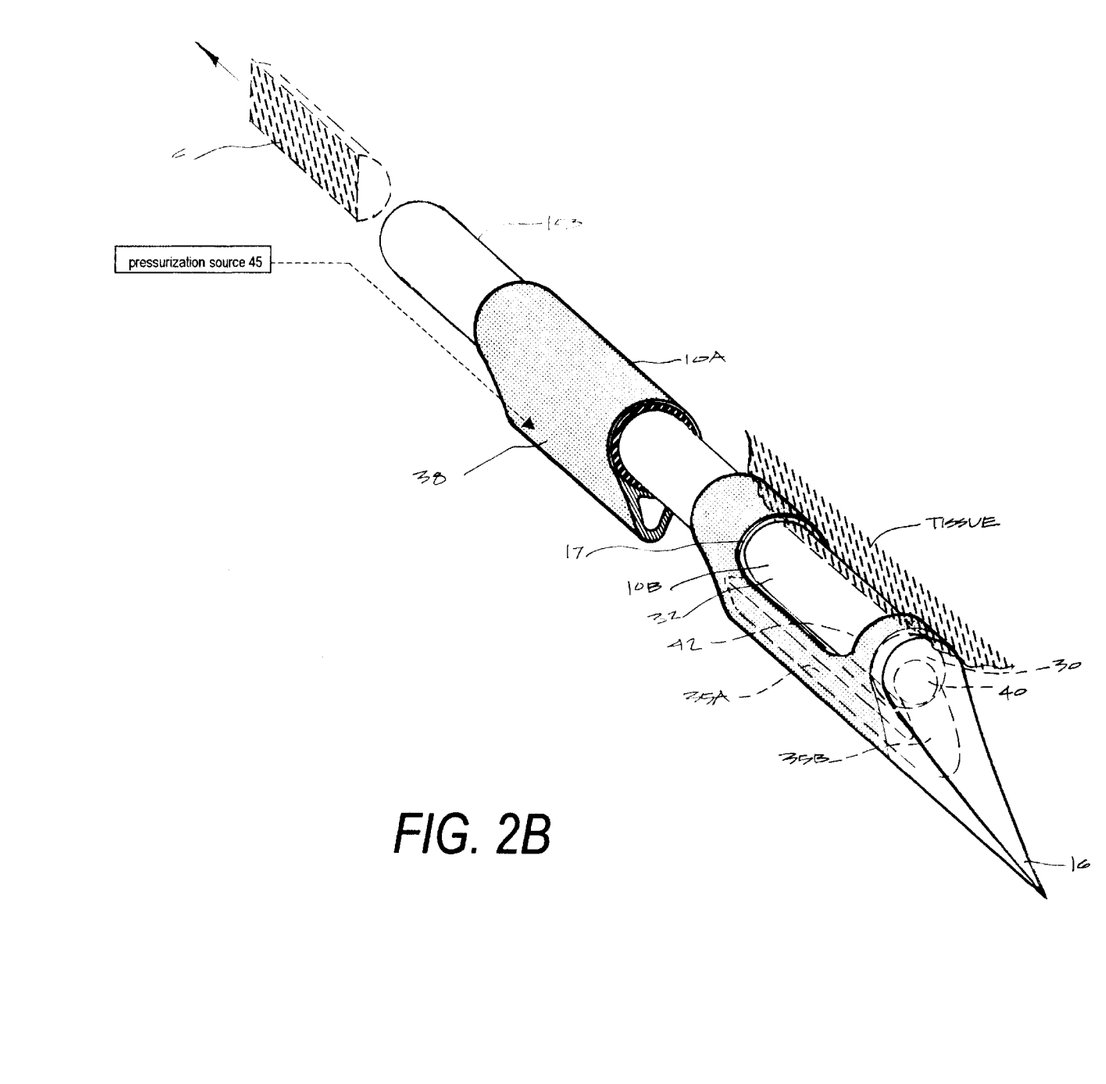
FIG. 2B is a view similar to FIG. 2A with the working end in a second position showing cutting of a tissue core.

FIG. 1 illustrates an exemplary biopsy probe or needle apparatus 5 of the present invention. The needle 5 comprises an elongate assembly of first outer sleeve member 10A and second interior sleeve member 10B that extend along longitudinal axis 12. The needle 5 has a distal working end 15 shown in FIG. 2A that is adapted for penetrating tissue with sip tip 16, and thereafter for cutting a core of tissue as will be described below. FIGS. 2A–2B show an enlarged cut-away view of working end 15 wherein it can be seen that outer sleeve 10A defines a side wall 17 around an interior passageway 20 that slidably carries the inner sleeve 10B.

The inner sleeve 10B has an interior passageway or bore 22 surrounded by a side wall indicated at 27. The needle assembly is adapted for grasping between the physician's fingers and therefore the inner and outer sleeves 10A and 10B are shown with (optional) gripping body portions indicated at 28a and 28b, respectively.

Referring to FIG. 2A, working end 15 is shown in detail wherein the interior pasageway 20 extends distally to a terminal chamber portion indicated at 30 that carries tissue-engaging opening 32 in a portion of side wall 17 of the outer sleeve 10A. The inner sleeve 10B that slides in interior passageway 20 has a sharp blade-type edge 33 at it distal circumference. It can be seen that by manual sliding of inner sleeve 10B in interior passageway 20 from a first retracted position (see FIG. 3) to a second extended position (see FIG. 3 phantom view), the blade edge 33 of inner sleeve will excise tissue that is engaged within the plane p defined by passageway 20 and the perimeter of opening 32. The distal sliding movement of the blade edge 33 from the first position to the second position will capture the tissue as a core c in the interior passageway 22 of the inner sleeve.

Figure 3:
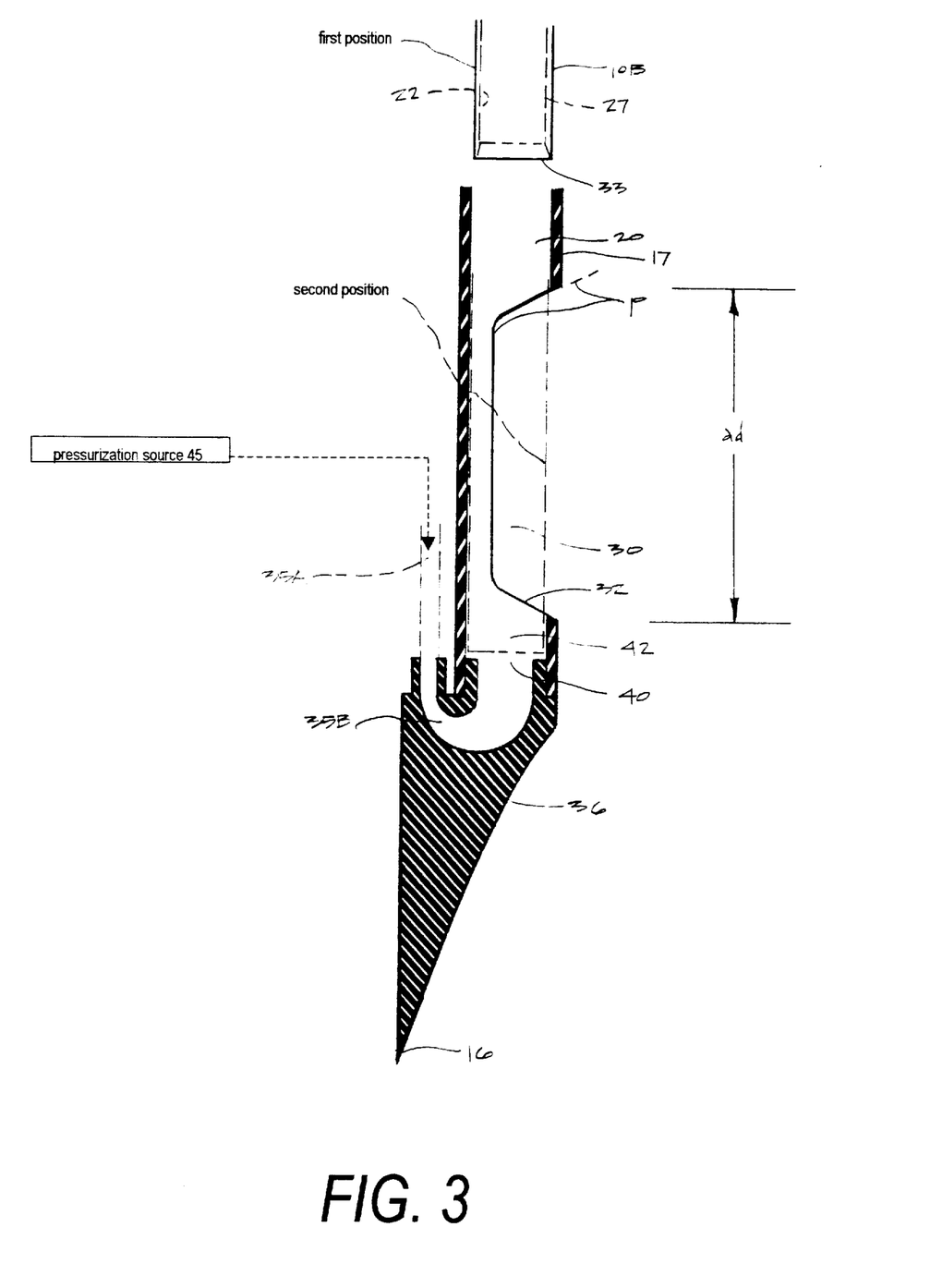
FIG. 3 is view of exemplary components of the working end of FIG. 2A

FIGS. 2A–2B and FIG. 3 illustrate the novel pressure-assisted tissue extraction component of the invention that is adapted for removing multiple cores of tissue from a single needle penetration. FIG. 2A shows that outer sleeve 10A carries a longitudinal inflow channel or passageway indicated at 35A for delivering a high pressure flow of fluid media m to the working end 15. Of particular interest, the high pressure flow is reversed in direction by a loop portion 35B of the inflow channel in a tip body indicated at 36. The inflow channel that comprises longitudinal channel portion 35A and loop portion 35B has a distal terminus 40 that is open to the distal end 42 of terminal chamber portion 30 of the interior passageway 20 wherein the excised tissue core c is captured FIG. 2B illustrates the core c being moved in the proximal direction in bore 22 of the inner sleeve under the high pressure flow that is reversed in direction by the loop portion 35B of the inflow channel at the distal end of the needle.

As can be seen in FIGS. 2A and 3, the needle assembly may be fabricated by using a suitable hypo tube for outer sleeve member 10A that has a diameter ranging from about 20 Ga. to 4 Ga. Preferably, the outer sleeve member 10A is from about 16 Ga. to 10 Ga. The axial dimension indicated at ad of the tissue-engaging opening 32 in the side wall of outer sleeve 10A may range from about 1.0 mm. in small diameter instruments to about 15.0 mm. in large diameter instruments. Preferably, the axial dimension ad of opening 32 ranges from about 2.0 mm to 10.0 mm. The distal end 37 of outer sleeve 10A is coupled to tip body 36 that may be of any suitable material such as metal or plastic that has a suitably sharp tip 16. The inflow loop indicated at 35B can be formed into tip body 36 by any suitable means of molding, casing or machine processes. FIG. 2A shows that a plastic extrusion indicated at 38 can provide the longitudinal inflow lumen 35A and be assembled around, or bonded to, outer sleeve 10A and connected to inflow loop 35B and tip body 36 (see FIG. 3).

FIG. 1 shows that a remote high pressure fluid pressurization source 45 is coupled to fitting 46 at the proximal end 48 of inflow channel 35A with any suitable flexible tubing. The pressurization source 45 may provide pressure ranging from about 1.0 psi to 500 psi. Preferably, the pressure used is from about 5.0 psi to 250 psi. The fluid media m that is delivered under pressure from source 45 is any suitable biocompatible gas or liquid, for example $CO_2$, sterile water or saline solution.

In practicing the method of the invention, the physician manually penetrates the needle of FIG. 1 into the patient's body to a first targeted site, for example, in a patient's breast under any type of imaging or localization techniques. While manually stabilizing the outer sleeve 10A, the operator then translates the inner sleeve 10B from the first position to the second position (see FIGS. 2A & 2B) to excise and capture a tissue core c in the pressurizable terminal chamber 30 and bore 22 of inner sleeve 10B. The terminal chamber 30 is pressurizable since the inner sleeve 10B closes off opening 32 in side wall 17 as shown in FIG. 2B. The operator then actuates the fluid pressurization source 45 by any suitable trigger means to cause pressurization of the terminal chamber 30 and bore 22 on the distal side of the tissue core c to expel the core in the proximal direction to proximal end 50 of the interior passageway 22 of the inner sleeve 10B (see FIGS. 1 & 2B). A basket-type collector or any other suitable vented collection structure indicated at 55 is coupled to proximal end 50 of interior passageway 22 to retain the core for biopsy or other diagnostic purposes. Of particular interest, the operator then may translate the inner sleeve 10B back to the first position from the second position, and repeat the above described steps to excise additional tissue cores. In normal operation, tissue will fall naturally into opening 32 in working end 15 and therefore be engaged by the cutting edge 33 of sleeve 10B. Optionally, the operator can use manual pressure on the patient's skin to compress tissue about working end 15 to insure that tissue is pressed into opening 32 and terminal chamber 30. The operator also may rotate the needle assembly 5 between repetitions of the above described steps to take tissue cores c that face in different directions at the targeted site. By practicing this method of the invention, a significant volume of tissue may be excised for biopsy purposes while making only on single needle penetration to the targeted site. It is no longer necessary to use multiple needle penetrations, as sometimes performed in prior art practices. The method of the invention still may be accomplished with a needle having a diameter in the range of 12 to 14 gauge, making the procedure very minimally invasive.

Figure 4:
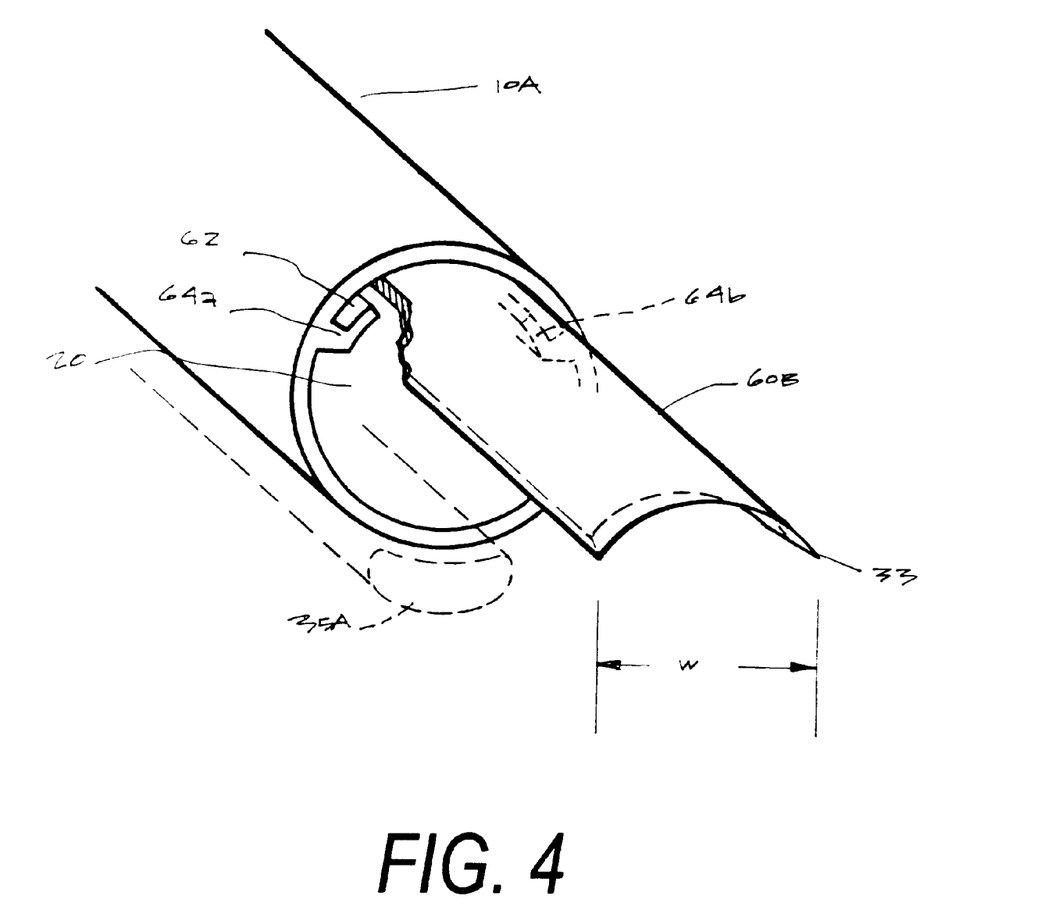
FIG. 4 is a sectional view of an alternative cutting member of the present invention.

FIG. 4 illustrates an alternative needle assembly 5 that operates as described above but utilizes an outer sleeve 10A that carries an alternative embodinent of inner cutting sleeve member indicated at 60B. FIG. 4 shows a section through a medial portion of the assembly in which outer sleeve 10A again defines wall 17 around interior bore 20 that extends to a terminal chamber 30 (not shown) and tissue-engaging opening 32 as described previously. Inflow passageway 35A is shown in phantom view. In this embodiment, the cutting sleeve or member 60B with blade edge 33 has a cross section defining width w that cooperates with a slot 62 or slot edge elements 64a and 64b within wall 17 of the outer sleeve 10A. The width w or radial arc of the blade is sufficient to cover the width of opening 32 (see FIG. 2A) when the blade member 60B is moved from a first retracted position to the second extended position (cf. FIGS. 2A & 2B) for the purposes of (i) excising the core of tissue, and (ii) closing off opening 32 to thereby by capture the tissue core in the closed off and sizable terminal chamber. The type of sleeve assembly shown in FIG. 4 may provide advantages for small diameter needles since the passageway 20 for extracting tissue is larger than would be the case if the cutting member were a tubular sleeve, as described previously.

2. Type "B" Pressure-Assisted Needle System for Stereotactic Localization

Figure 5:
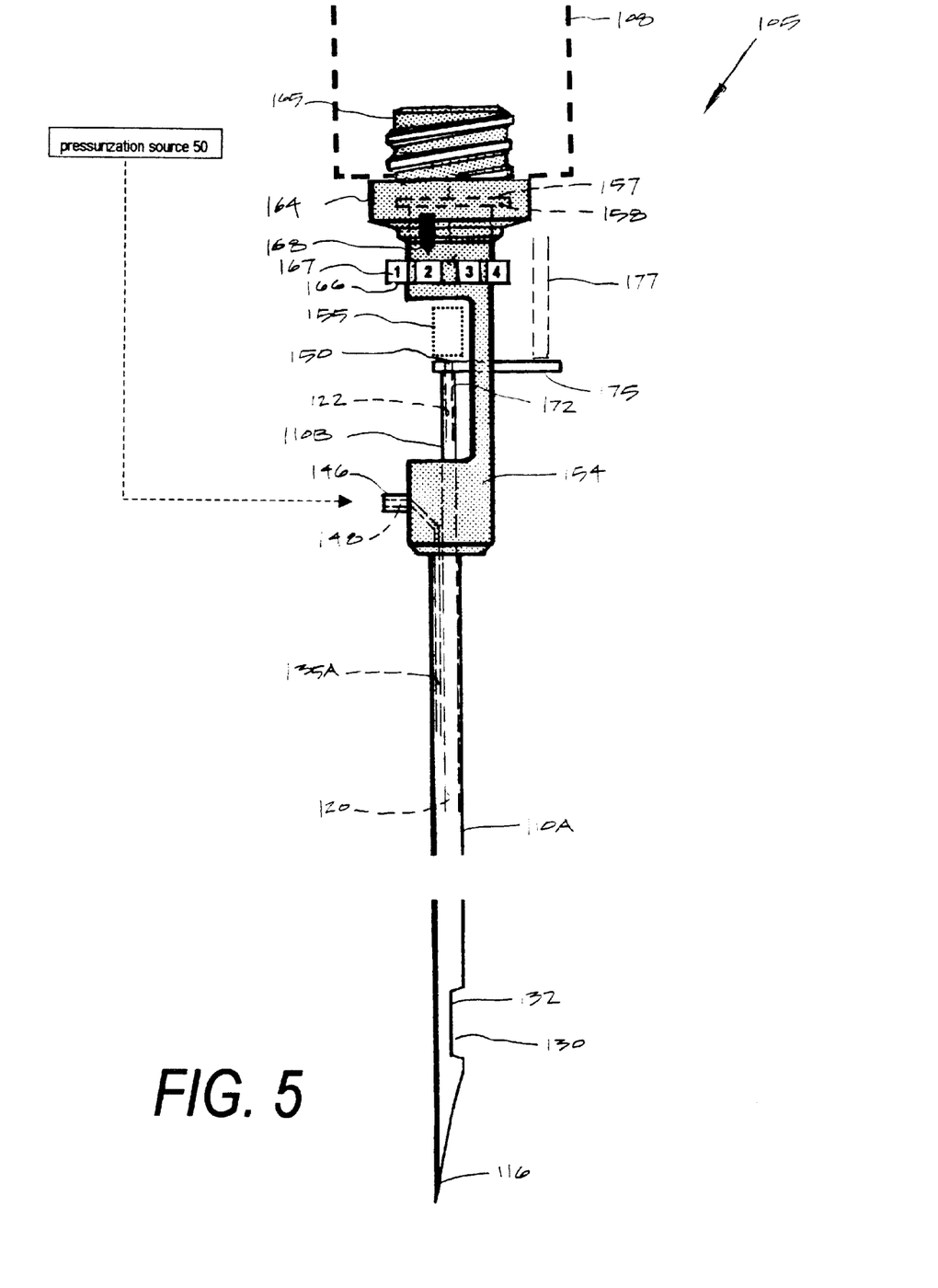
FIG. 5 is an elevational view of an exemplary Type "B" system adapted for use by a stereotactically-guided stage of a breast biopsy apparatus.

FIG. 5 illustrates an exemplary Type "B" biopsy needle system 105 of the present invention that functions as the Type "A" system except that is adapted for automated penetration into the patient's body utilizing stereotactic localization of the needle tip. The elements of the Type "B" system that are the same as the Type "A" system have the same reference numerals +100.

In this embodiment, the needle assembly 105 is adapted for detachable coupling to a moveable stage 108 that cooperates with a mammography system table (not shown). For example, Lorad/Trex manufactures a digital spot mammography (DSM) system, with a motorized, programmable biopsy stage that can localize insertion of a needle with reference to x-y-z axes (see Trex Medical Corporation, 37 Apple Ridge Rd., Danbury, Conn. 06810). The stage 108 is moveable to automate insertion of the working end 115 of needle 105 within a targeted lesion.

As shown in FIG. 5, the needle assembly again comprises outer sleeve 110 A that carries slidable cutting sleeve 110B in interior bore 120 of the outer sleeve. The inner sleeve 110B has a longitudinal bore 122 therein for extracting tissue. The needle assembly 105 has distal tip 116 and tissue-engaging opening 132 as described above. Inflow channel 135A has fitting 146 at its proximal end 148 in distal body member 154 of the apparatus. The proximal end 150 of the tissue-exacting bore 122 of the inner sleeve 110B is coupled to tissue-receiving structure or basket 155.

FIG. 5 shows that outer sleeve 110A has its proximal end 156 fixed in distal body member 154. The distal body member 154 has a round, keyed proximal end 157 that allows it to rotate within a receiving bore portion 158 of proximal body member 164 as can be seen in FIG. 5. The proximal body member 164 is shown with exemplary threaded portion 165 for detachable coupling to stage 108 of the stereotactic assembly.

The distal body member 154 that carries outer sleeve 110A is provided with a grip portion 166 that may can carry indicator numbers 167 for rotating the distal body member 154 relative to fixed proximal body member 164 and indicator arrow 168. By this means, successive tissue cores may be taken with tissue-engaging opening 132 facing at various predetermined angles within the targeted tissue. By taking cores at 4 to 8 different radial angles, a substantial total tissue volume may be removed for biopsy or prophylactic purposes. Further, each of several cores retrieved from the tissue-receiving structure 155 can separately marked or numbered to thereafter allow re-assembly of the cores into their original orientations in a graphic image of the excised tissue volume in a graphics software system. Each core, for example, can undergo a rapid frozen section biopsy. Such a graphic image of the several cores and the biopsy analyses can direct further core sampling with the needle assembly rotated in a particular direction if suspicious tissue characteristics are found in some cores and not others. By using a larger diameter needle assembly, for example a 5.0 mm. outer sleeve 110A, successive core removals may provide an automated form of lumpectomy treatment The use of rapid biopsy techniques and the creation of software-based images again can direct the operator to rotate the needle assembly 105 to remove more tissue in a particular angular direction to insure safe margins around a suspicious lesion that is targeted for removal.

As can be seen in FIG. 5, the proximal end 172 of inner sleeve 110B is fitted with a handle member indicated at 175. The handle member 175 is adapted for manual actuation to move inner sleeve 110B relative to outer sleeve 110A to thereby move the working end between the first and second position as shown in FIGS. 2A & 2B. Alternatively, the actuation of inner cutting sleeve 110B may be caused by a spring that will rapidly advance the cutting sleeve within the outer sleeve 110A (not shown). As another alternative, a motorized or otherwise mechanically actuated push-rod 177 phantom view in FIG. 5) may be provided within stage 108 to automate the actuation of sleeve 110B to excise the tissue core.

Figure 6:
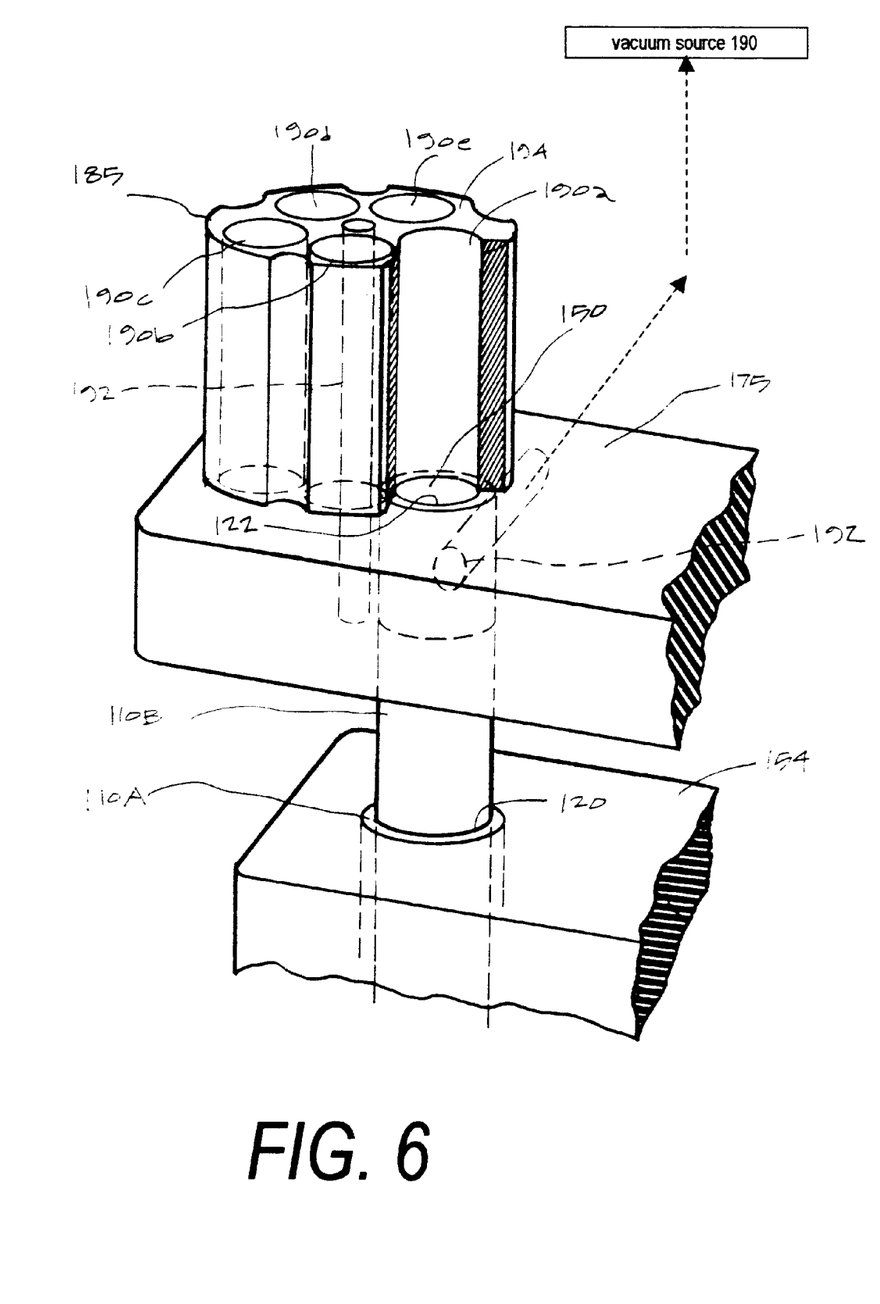
FIG. 6 is a perspective view of a tissue-collecting strucre of the present invention for receiving a plurality of tissue cores.

FIG. 6 shows an alternative embodiment of tissue-receiving cylinder structure indicated at 185 that can be fitted to the needle assembly of FIG. 5. The cylinder structure 185 provides separate basket chamber portions 190a–190e for receiving the successive cores of excised tissue. The cylinder structure 185 is manually rotatable (or automated to rotate) about, and removable from, pin 192 and is carried by handle portion 175 of a needle assembly similar to that of FIG. 5. Each chamber 190a–190e has a diameter that cooperates with diameter of tissue-extracting bore 122 of sleeve 110B. As can be seen in FIG. 6, the cylinder structure 185 is rotated so that each chamber 190a–190e can be aligned with the proximal end 150 of bore 122 of sleeve 110B. The proximal face 194 of the cylinder structure 185 or the walls of cylinders 190a–190e carry vent openings of a selected dimension to allow release of media m that expels the tissue cores from the proximal end 150 of bore 122 (not shown). In operation, the needle assembly 105 can be rotated so that cores are taken facing a number of different pre-set angular directions in the targeted tissue. Then, the cylinder structure 185 can be rotated to collect and identify each tissue core in a separate chamber 190a–190e. The cylinder 185 is removable from the needle assembly for ease of removing the tissue cores. It should be appreciated that any number of chambers are possible, and the cylinder structure 185 with five chambers is shown for convenience only. Preferably, the cylinder structure 185 would have from 4 to 8 chambers to cooperate with 4 to 8 angular pre-sets associated with the rotation of the needle assembly 105 in the stage 108 of the stereotactic assembly.

FIG. 6 further shows another optional component of the invention that comprises a vacuum source 190 in fluid communication with internal bore 122 of inner sleeve 110B via port 192 for suctioning tissue into the opening 132 of the outer sleeve 110A prior to excising the tissue core. As can be easily understood, a manual or automated valve means (not shown) may be provided for closing the open proximal end 150 of interior bore 122 to cause all vacuum forces to be directed from vacuum source 190 to the distal working end of the needle assembly, rather than the proximal end of bore 122 and the basket assembly 155 for collecting tissue (see FIG. 5).

Figure 7:
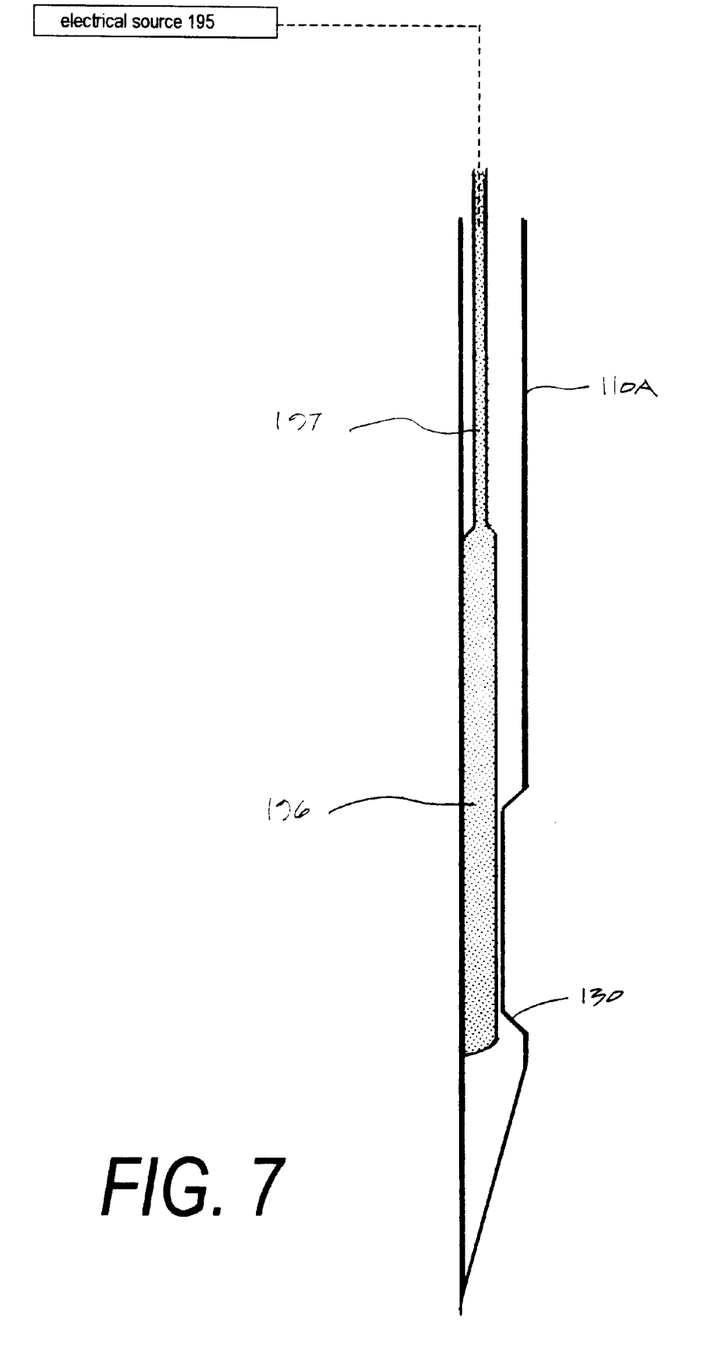
FIG. 7 is a side view of an alternative needle assembly with an electrode for cauterizing tissue.

FIG. 7 shows optional electro-cauterizing means of the invention wherein an Rf (radiofrequency) electrical source 195 is coupled to a mono-polar electrode 196 by lead portion 197 on a portion of outer sleeve 110A. By actuation of the electrode in cooperation with a groundpad, the operator can cauterize the treatment site and the needle track after the tissue removal procedure is complete by delivering Rf energy while rotating the needle. The exemplary electrode 196 in FIG. 7 is a thin film electrode insulated from, and bonded to, the outer surface of sleeve 110 A. It should be appreciated that the invention also may provide paired bi-polar electrodes on the surface of sleeve 110A. As another alternative, the entire outer sleeve 110A may serve as an electrode.

It should be appreciated that the present invention has been described in detail in particular embodiments suited for breast biopsy and removal of tissue in a minimally invasive procedure. Similar devices and working ends may be used for tissue removal in any part of a patient's body. For example, the probe may be provided with a rounded working end tip with the tissue-receiving opening and cooperating blade member adapted for cutting, trimming or shaping tissue in an arthrosopic procedure (not shown). The sleeve assembly thus would be suitable for introduction through a trocar sleeve or other cannula In such an endoscopic tissue-cutting instrument, an optional programmable controller can be provided to control the duration of intervals of pressurized inflows from pressurization source 45, as well the level of suction provided by an optional vacuum source 190 (cf. FIG. 6). Further, the controller also can be coupled to an automated mechanism similar to push-rod 177 of FIG. 6 to control the repetitions and seeds of moving the cutting member between the first and second positions. Various mode of operation are possible with such a controller. For example, the controller can modulate or control operational parameters of the assembly, including (i) actuation for the inner cutting member; (ii) pressured levels and on-off intervals of pressure source 45; and, vacuum levels and on-off intervals of the optional vacuum source. Additionally, the surgical system may be provided with feedback sensing systems coupled to the controller for sensing operational parameters of the system while in use. The sensing system, for example, can be adapted to sense a selected parameter such as: a selected pressure level in the inflow lumen; changes in the pressure level or a rate of change in the pressure level; a selected vacuum level in the interior tissue-extracting passageway; a change in the vacuum levels or a rate of change in the vacuum levels. Upon detection of a selected parameter, an optional step in the method of practicing the invention is then for the controller to be programmed to modulate the operational parameters describer previously.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. A method for excising and removing a tissue volume from a targeted site in the interior of a patient's body, comprising the steps of:
   (a) providing an elongate sleeve member that defines a wall around an internal passageway, said internal passageway having an open proximal end and a distal terminal chamber, and an opening in the wall of said terminal chamber for engaging tissue therein;
   (b) introducing a distal end of said sleeve member to the targeted site;
   (c) actuating a blade member from a first position to second position across said opening in the wall of said terminal chamber thereby excising a volume of tissue engaged in said opening;
   (d) wherein the actuation of the blade member in step (c) contemporaneously closes off said opening; and
   (e) delivering a high pressure flow of a selected fluid media to a distal end of said terminal chamber thereby expelling the excised tissue volume in the proximal direction in said internal passageway to an open end thereof.

2. The method of claim 1 wherein the high pressure fluid flow of step (e) enters said terminal chamber at a location distal to the excised tissue volume captured therein.

3. The method of claim 1 wherein said fluid media is a biocompatible gas or biocompatible liquid.

4. The method of claim 1 wherein a pressurization source provides said high pressure flow in the range of 1 to 500 psi.

5. The method of claim 1 wherein a pressurization source provides said high pressure flow in the range of 5 to 250 psi.

6. The method of claim 1 wherein the sleeve member has a needle-type distal tip and step (b) comprises penetrating said sleeve member through tissue to the targeted site.

7. The method of claim 1 wherein the steps (c) through (e) are repeated to excise and remove successive tissue volumes.

8. The method of claim 7 wherein further comprsing the step of rotating the sleeve member a selected angular dimension between the repetition of steps (c) through (e).

9. The method of claim 1 further comprising the step of receiving the tissue volume within a tissue-collecting structure at the proximal end of said internal passageway.

10. The method of claim 9 further comprising the step of receiving successive tissue volumes in separate chamber portions of a tissue-collecting structure at the proximal end of said internal passageway.

11. The method of claim 1 further comprising the step of cauterizing tissue with at least one electrode incorporated into the sleeve member.

12. The method of claim 1 wherein prior to step (c), the additional step of applying a vacuum force to said internal passageway to suction tissue into said opening.

13. A surgical device for excising and extracting soft tissue volumes, comprising:
   (a) an elongate member carrying a looped inflow-outflow passageway system comprising:
      (i) an outflow passageway extending between a proximal end and a distal terminal chamber;
      (ii) an inflow passageway extending between a proximal end and a distal terminus;
   (b) wherein the distal terminus of the inflow passageway communicates with the distal terminal chamber of the outflow passageway;
   (c) a tissue-receiving opening in a wail surrounding said terminal chamber for receiving a tissue volume, wherein said opening has a first open position for receiving tissue and a second closed position for extracting tissue;
   (d) a moveable blade member carried by said elongate member for excising the tissue volume in said tissue-receiving opening and thereby altering said opening between said first open position and said second closed position; and
   (e) a pressurization source coupled to said proximal end of the inflow passageway.

14. The device of claim 13 further comprising coupling means for coupling a proximal end of the elongate member to a moveable stage of a stereotactic needle localizing assembly.

15. The device of claim 13 further comprising a tissue-collecting structure coupled to a proximal end of said outflow passageway.

16. The device of claim 15 wherein said tissue-collecting structure has a plurality of chamber portions for separately receiving tissue volumes.

17. The device of claim 13 further comprising a vacuum source coupled to a proximal end of said outflow passageway.

18. The system of claim 13 further comprising a controller for controlling an operational parameter of the system selected from the class comprising: actuation for the cutting member, the pressure level and on-off intervals of pressure delivery from a pressurization source; and, the vacuum level and on-off intervals of a vacuum source.

19. The system of claim 13 further comprising a sensing system coupled to said controller for feedback control of said operational parameters, said sensing system capable of sensing parameters selected from the class comprising: a pressure level in the inflow lumen; a change in said pressure level or a rate of change in said pressure level; a selected vacuum level in the interior tissue-extracting passageway, a change in said vacuum level or a rate of change in said vacuum levels.

* * * * *